(12) United States Patent
Merchant et al.

(10) Patent No.: US 11,497,684 B2
(45) Date of Patent: Nov. 15, 2022

(54) RECONSTITUTION VIAL MIXING APPARATUS

(71) Applicant: SUMMIT INTERNATIONAL MEDICAL TECHNOLOGIES, INC., Franklin, MA (US)

(72) Inventors: Michael A. Merchant, Franklin, MA (US); Hsi Chin Tsai, Franklin, MA (US)

(*) Notice: Subject to any disclaimer, the term of this patent is extended or adjusted under 35 U.S.C. 154(b) by 286 days.

(21) Appl. No.: 16/575,442

(22) Filed: Sep. 19, 2019

(65) Prior Publication Data

US 2020/0330326 A1   Oct. 22, 2020

Related U.S. Application Data

(60) Provisional application No. 62/879,455, filed on Jul. 27, 2019, provisional application No. 62/834,915, filed on Apr. 16, 2019.

(51) Int. Cl.
  *A61J 1/20* (2006.01)
(52) U.S. Cl.
  CPC .............. *A61J 1/2089* (2013.01); *A61J 1/201* (2015.05); *A61J 1/2058* (2015.05)
(58) Field of Classification Search
  CPC ........ A61J 1/2089; A61J 1/201; A61J 1/2058; A61J 1/2037; A61J 1/10; A61J 1/2055
  See application file for complete search history.

(56) References Cited

U.S. PATENT DOCUMENTS

| | | | |
|---|---|---|---|
| 4,581,014 A | 4/1986 | Millerd et al. | |
| 8,551,067 B2 | 10/2013 | Zinger et al. | |
| 10,772,798 B2 * | 9/2020 | Lev | A61J 1/10 |
| 2003/0191445 A1 * | 10/2003 | Wallen | A61M 5/1408 |
| | | | 604/411 |
| 2011/0004184 A1 * | 1/2011 | Proksch | A61J 1/20 |
| | | | 604/407 |
| 2016/0166824 A1 | 6/2016 | Lev et al. | |

* cited by examiner

*Primary Examiner* — Jason K Niesz
(74) *Attorney, Agent, or Firm* — Armis IP Law, LLC (57) ABSTRACT

A medicinal vial reconstitution and IV dispensing device includes a bifurcated receptacle adapted to engage a medicinal vial, and a valve or barrier for selectively opening and closing the medicinal vial from fluidic communication with the patient IV line. The reconstitution device mixes medication with saline solution from an IV bag through a dedicated channel. The reconstitution device receives a medication vial containing the powdered medication. The reconstituted medication is then passed back into the IV bag for uniform mixing. A flow control element ensures fluid flow only from the vial to the bag. Once mixed, the reconstituted medication achieves a desired concentration in the IV bag. The (now medicated) saline solution in the IV bag is dispensed back through the reconstitution device via an IV line to the patient, and the flow control element redirects fluid only to the IV line and prevents any backflow with the vial.

18 Claims, 7 Drawing Sheets

RECONSTITUTION VIAL MIXING APPARATUS

RELATED APPLICATIONS

This patent application claims the benefit under 35 U.S.C. § 119(e) of U.S. Provisional Patent Application Nos. 62/834,915, filed Apr. 16, 2019, entitled "RECONSTITUTION VIAL MIXING APPARATUS," and 62/879,455, filed Jul. 27, 2019, entitled "DUAL CHANNEL VIAL MIXING APPARATUS," both incorporated herein by reference in entirety

BACKGROUND

IV (Intravenous) lines are commonly used for hydration and medication of patients. The IV line establishes a fluid flow to the patient bloodstream for maintaining a bodily fluid balance, and also provides a convenient medium for medicinal transport, since the IV fluid (typically saline solution) defines a regular flow into the bloodstream from a saline solution bag and is preferable to subjecting the patient to an additional needle injection. IV medications may be mixed into the saline solution bag for delivery with the saline solution. Medications are generally delivered in a concentrated liquid or powder form, and are introduced into the saline solution bag through an access port. Powdered medications need to be reconstituted by mixing with liquid prior to being introduced into the IV bag. The quantity of concentrated medication is generally based on an expected quantity of saline solution for providing an appropriate dosage and introduction rate of the IV delivered medication.

SUMMARY

A medicinal vial reconstitution and IV dispensing device includes a receptacle adapted to engage a medicinal vial, and a valve or barrier for selectively opening and closing the medicinal vial from fluidic communication with the patient IV line. The valve or barrier imposes a bifurcated, dual channel construction in the device that prevents fluidic mixing between the reconstitution and delivery phases. The reconstitution device mixes powdered medication with saline solution from an IV bag. The reconstitution device receives a medication vial containing powdered medication or drugs, and allows controlled dispensing of a small amount of saline solution from an IV bag into the reconstitution vial (vial). The dispensed saline solution is agitated to mix with the powder medication in the vial for reconstituting the medication into a liquid form. The reconstituted medication is then passed back into the source IV bag for uniform mixing. A flow control element ensures fluid flow only from the vial to the bag. Once mixed, the reconstituted medication combined with the volume of saline solution in the IV bag achieves a desired concentration. The (now medicated) saline solution in the IV bag is dispensed through the reconstitution device via an IV port connecting to the IV line to the patient, and the flow control element redirects fluid only to the IV line and prevents any backflow or fluid communication with the vial.

Configurations herein are based, in part, on the observation that conventional reconstitution devices have a fixed 3-way fluidic communication between the medicinal vial, IV bag, and IV line. Unfortunately, conventional approaches and devices for IV reconstitution can result in incomplete reconstitution and inadequate mixing. Powdered medication can remain unmixed, or partially mixed, in the vial or in a transfer channel leading back into the vial. Incomplete mixing can affect the concentration of medication in the IV flow to the patient. Residual, unmixed, or partially mixed powder remaining in the vial can result in under concentrated medication, or an overly concentrated mix remaining in the transfer channel may release suddenly into the IV stream, causing a "burst" or "bolus" of medication in the IV line and causing overconcentrated delivery. Accordingly, configurations herein substantially overcome the shortcomings of conventional reconstitution devices by providing a valve connection and/or dual transfer channels to the medication vial, providing fluidic separation between the transfer channel and the IV bag/IV line. Distinct phases of reconstitution, mixing and delivery can therefore be established for mitigating residual medication that can result in a non-uniform IV delivery stream.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

The disclosed reconstitution device takes the form of an Intravenous (IV) connector adapted to be disposed in an IV line for delivering saline solution or similar IV fluid containing the reconstituted medication to a patient via an IV line. Reconstitution involves extracting a small portion of the saline solution from the IV bag into the vial, reconstituting the medication in a mixture of the saline solution and concentrated medication, then passing the reconstituted mixture back through the dedicated dual channel IV connector to mix with the full quantity of saline solution in the IV bag. The same IV connector also leads to the patient IV line, and the reconstituted medication flows back out of the bag but passes only to the patient IV line, and does not "backwash" or flow into the vial due to a flow control element directing all the medicated IV saline solution only to the IV line.

Figure 1:
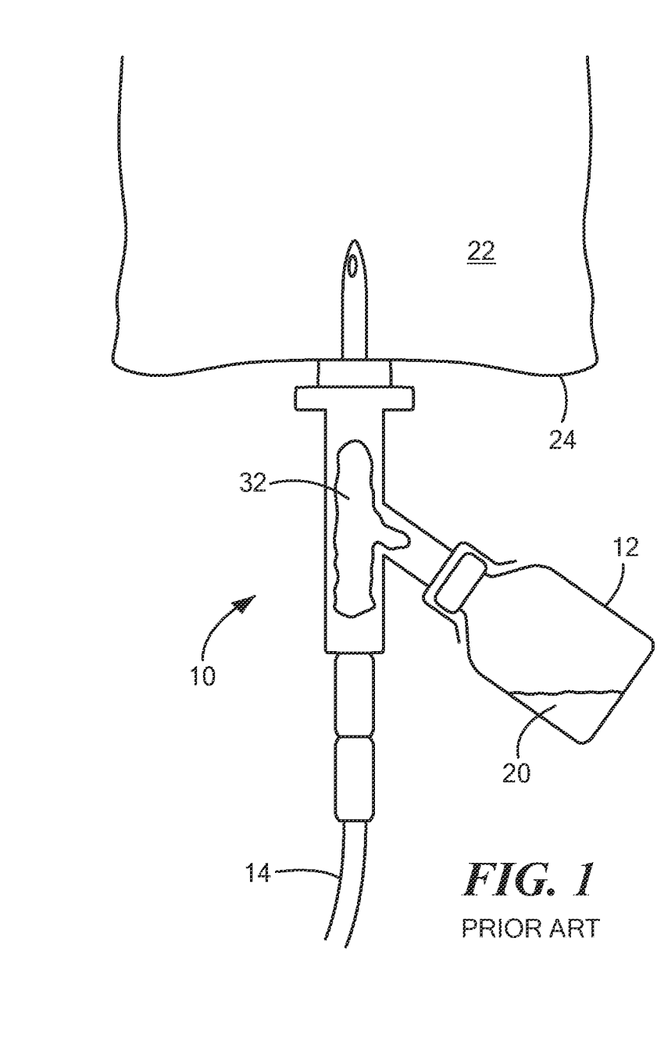
FIG. 1 is a prior art reconstitution mixing device.

FIG. 1 is a prior art reconstitution mixing device. Referring to FIG. 1, a conventional delivery device 10 allows medication delivery from a conventional medication vial 12 to a patient though a conventional IV line 14. Concentrated medication 20 in the medication vial 12 needs to be reconstituted by mixing with saline solution 22 or other delivery fluid from an IV bag 24. Saline solution 22 from the IV bag 24 is mixed with the medication 20 by forcing the saline solution into the vial 12 through a dedicated flow channel, and returning the concentrated medication to the IV bag 24 as a conventional mixture of saline solution and medication. The quantity of concentrated medication 20 is intended for mixing with an entire volume of saline solution 22 in the IV bag 24 for proper administration.

A mixing region 32 is defined in the conventional delivery device 10 at a fluid junction of the medication vial 12, the IV bag 24, and the IV line 14. Medication is expected to pass through the conventional mixing region at least twice- once as the concentrated medication exits the vial 12 and travels to the IV bag 24, and again as the reconstituted medication (meaning mixed at a correct or expected concentration) passes from the IV bag 24 to the conventional IV line 14. Since the conventional mixing region 32 connects each of the vial 12, IV bag 24, and IV line 14, concentration irregularities can result in the mixing region 32 which cause the conventional IV line 14 to deliver medication at higher or lower concentrations than the expected concentration.

Figure 2:
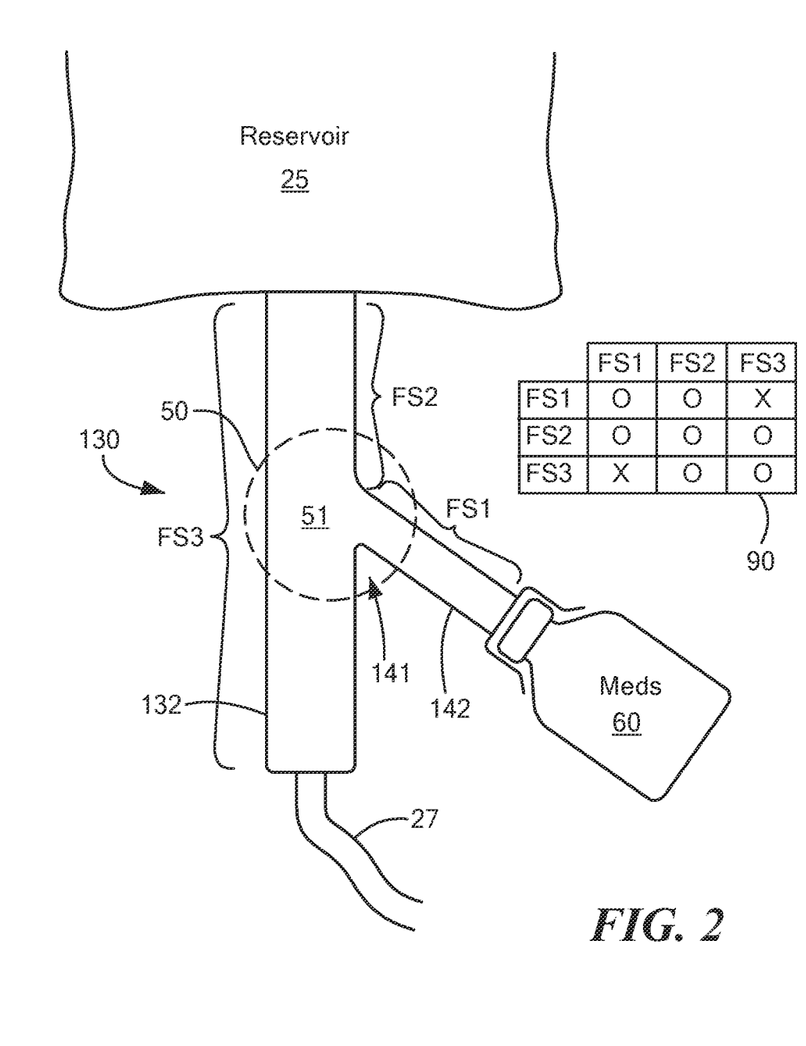
FIG. 2 show fluidic flow control in the disclosed reconstitution device.

FIG. 2 shows fluidic flow control in the disclosed reconstitution device. In the reconstitution device 100, saline solution used for reconstituting the medication is also used for delivering the medication. A small amount of saline solution is transferred to the vial for reconstitution through a dedicated flow channel, resulting in a concentrated medication mixture or solution in the vial. This concentrated liquid in the vial is then transferred back into the IV bag where it mixes with the remaining saline solution to result in a proper concentration for patient delivery. During the reconstitution step, an indefinite and possibly harmful concentration of powdered or liquid medication exists in the vial. It is beneficial if this intermediate concentration is directed for combination with the IV bag prior to any release into the patient IV line. Otherwise, portions of concentrated and/or unmixed medication may inadvertently remain in the mixing region 32 and pass to the patient IV line prior to complete mixing and dilution with a full volume of saline solution in the IV bag. The flow control imposed by the valve or barrier imposes a divided, dual channel construction in the device that prevents fluidic mixing between the reconstitution and delivery phases.

Accordingly, the flow control element in the IV connector defines a plurality of fluidic flow segments though the IV connector, such that the medicinal fluid traverses the fluidic flow segments in a predetermined sequence. The predetermined sequence directs the flow of saline solution, reconstituted medication, and properly diluted medication between a medication source 60 such as a vial, a fluid reservoir 25 such as a saline solution bag, and an IV line 27 or IV tubing to a patient. A first flow segment FS1 extends from a transfer channel 142 ingress to the IV connector 130. A second flow segment FS2 extends from the transfer channel 142 into the fluid reservoir 25, and a third flow segment FS3 extends from the fluid reservoir 25 to the patient IV line 27 through the IV connector 130, such that the flow control element is disposed for directing fluid from the first flow segment to the second flow segment prior to the fluid traversing the third flow segment. A fluid communication table 90 shows allowed fluid paths, and indicates that medication fluid cannot pass directly from FS1 to FS3, thus forcing all fluid thorough the saline solution bag for proper concentration.

A flow control element 50 is disposed at or near the junction 51 of the flow segments FS1 . . . FS3 for moderating fluid flow though the junction 51 for enforcing proper concentration of delivered medicine. As a result of the flow control element 50, the second FS2 and third flow segments FS3 travel in opposed directions though the IV connector 130. The flow control element 50 may be any suitable fluidic barrier suitable for enforcing the flow segments and fluidic communication between the flow segments, the receptacle, IV bag and patient IV line 127 via the IV connector. In particular configurations, the flow control element may be a valve or partition for directing and/or restricting the flow segments.

Figure 3:
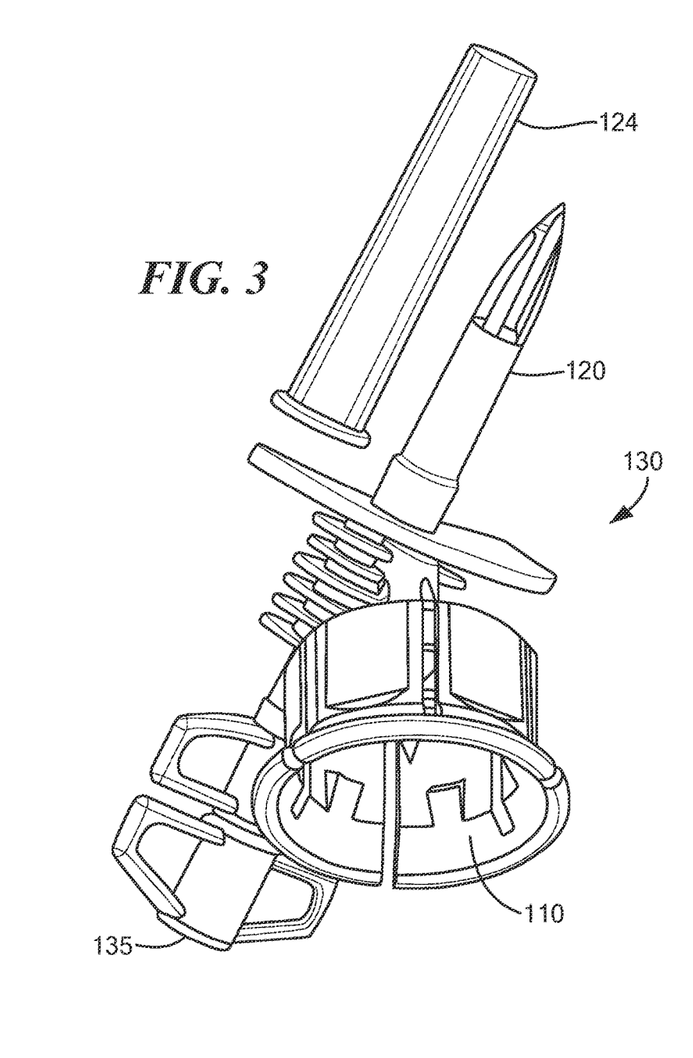
FIG. 3 shows a perspective view of the reconstitution device of FIG. 2.

FIG. 3 shows a perspective view of the reconstitution device of FIG. 2. Referring to FIGS. 2 and 3, the IV connector 130 includes an IV spike 120 adapted for insertion into an IV bag defining the reservoir 25, a cap 124, a receptacle 110 for engaging a medicinal vial containing the medication 60, and an IV outlet 135 including one or more IV tabs 137 for engagement by the patient IV line 27. In operation, the IV connector 130 facilitates IV delivery of a vial based medication concentration requiring reconstitution.

Figure 4:
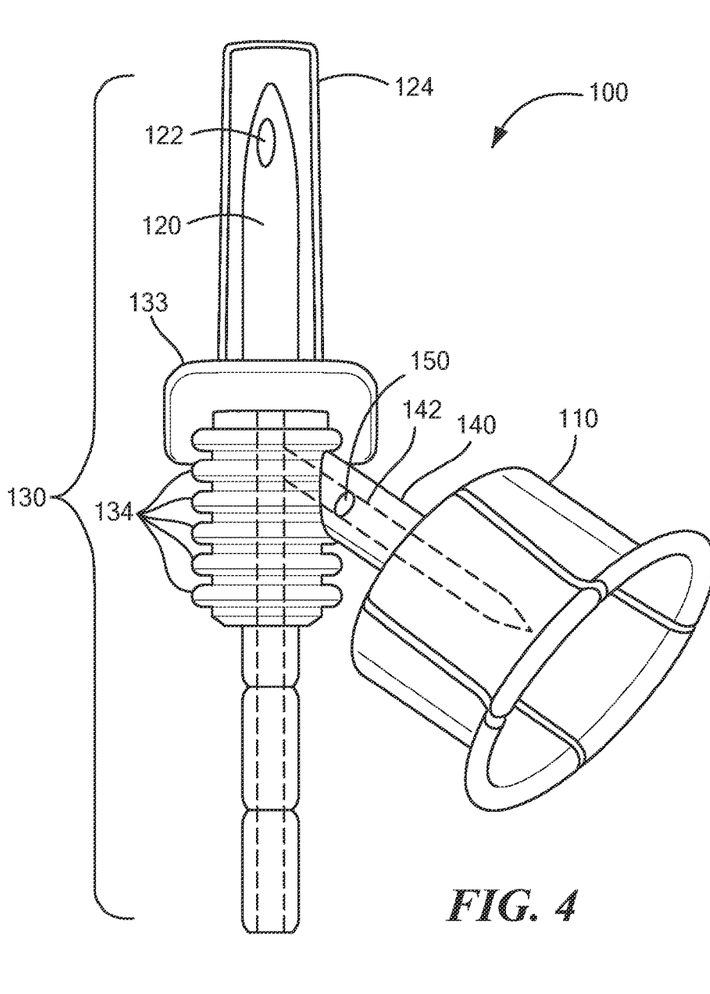
FIG. 4 a cutaway view of the reconstitution device of FIG. 2 including a flow control element.

FIG. 4 a cutaway view of the reconstitution device of FIG. 2 including the flow control element 50. Referring to FIGS. 2-4, the medicinal vial reconstitution and dispensing apparatus 100 includes a receptacle 110 adapted to engage a medicinal vial, and an intravenous (IV) connector 130 adapted for inline connection to a patient IV line. The IV connector 130 is adapted for transport of medicinal fluids to a patient via an aperture 122 or passage in a tapered end defining an IV spike 120, and remains covered by the cap 124 until just prior to use. A bifurcated junction body 140 extends from a longitudinal side of the IV connector to the receptacle 110, and has a transfer channel 142 adapted for fluidic communication between the receptacle 110 and the IV connector 130 for transferring liquids between the vial and IV connector 130. The flow control element 50 defines a selective closure such as a valve 150 or other fluid retention and/or interference mechanism in the bifurcated junction body 140 that allows selectively opening and closing of the transfer channel 142 for sealing the medicinal vial from an IV channel 132 through the IV connector 130. Ribs 134 around the junction 51 of the transfer channel 142 and IV channel 132 provide reinforcement for the transfer channel valve 150, discussed further below. A flange 133 region extending outward from the connector 130 may have a textured or dimpled surface to facilitate a frictional grip during IV bag insertion.

In FIG. 4, the bifurcated junction body 140 extends from the IV connector 130 to the receptacle 110, and encapsulates the transfer channel 142 for fluidic communication between the receptacle 110 and the IV connector 130 for transferring liquids between the vial and IV connector 130. The flow control element 50 enforces a controlled flow path through the IV connector 130, such that the controlled flow path directs fluid from the transfer channel 142 to the fluid reservoir 25 before passing to the patient IV 27 line through the IV connector. The transfer channel valve 150 disposed along the transfer channel 142 defines the flow control element 50. In this arrangement, the flow control element 50 selectively impedes fluidic flow through the transfer channel 142 for preventing unwanted flow to the patient IV line 27, discussed further below. Therefore, the second flow segment FS2 and the third flow segment FS3 pass thorough the IV connector 130 and into and out of the reservoir 25. The flow control element 50 therefore directs a fluidic path from the vial through the reservoir 25 prior to fluidic flow into the patient IV line 27.

Figure 5:
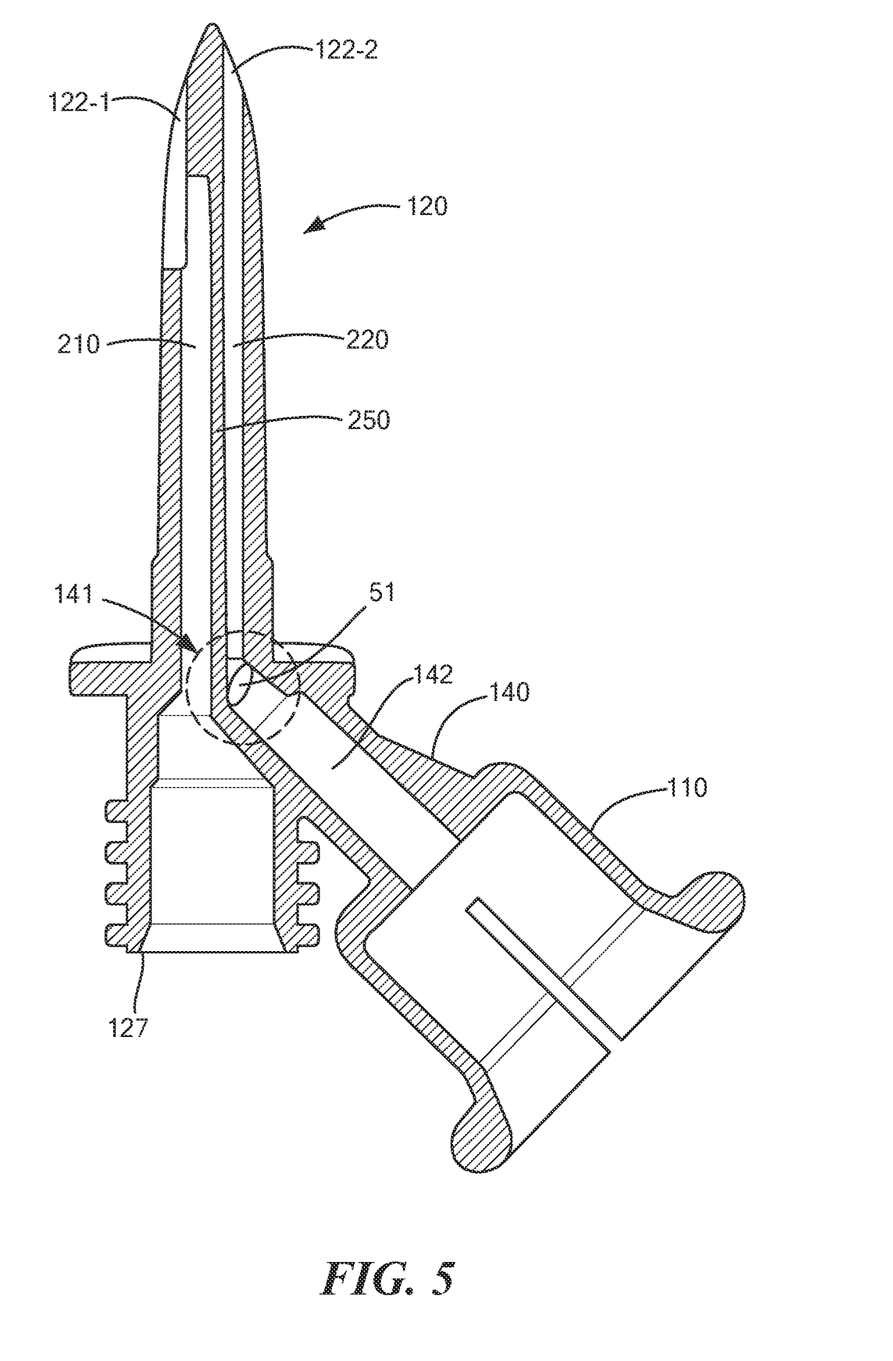
FIG. 5 shows a cutaway view of the reconstitution device of FIG. 2 including an alternate flow control element.

FIG. 5 shows a cutaway view of the reconstitution device of FIG. 2 including an alternate flow control element 50. Referring to FIGS. 2 and 5, the flow control element 50 includes a partition 250 that defines a dual channel approach in the device of FIG. 2 for managing the flow segments FS1 . . . FS3. Referring to FIGS. 2-5, a first channel 210 extends from the bag spike 120 to the patient IV line 27 via an IV port 127, and defines flow segment FS3. A second channel 220 extends from the bag spike 120 to the junction 51, defining flow segment FS2. As a result of the partition 250 extending to the junction 51, the second channel 220 connects only to the transfer channel 142, and does not permit fluidic communication with the first channel 210 or the patient IV line 27, thus defining flow segment FS1 from the receptacle 110.

The bifurcated junction body 140 encloses the transfer channel 142 defining the first flow segment FS1, connecting with the second channel 220 to define flow segment FS2 at bifurcation 141. The IV connector 130 includes the IV bag spike 120 adapted for insertion into an IV bag 125 defining the fluid reservoir 25. The second channel 220 is therefore adapted for fluidic communication between the receptacle 110 and the IV bag 125 via the IV bag spike 120. The first channel 210 is adapted for transferring liquids between the IV bag 125 and IV port 27 via the IV bag spike 120 when inserted into the IV bag.

Based on the partition 250, the IV connector 130 has separate, dual channels 210, 220 defined by the flow control element 50, such that each channel corresponds to one of the second or third flow segments. In this arrangement, the flow control element 50 divides fluid flow between an ingress channel and an egress channel to the fluid reservoir 25. The flow control element 50 defines a first channel 210 and a second channel 220 through the IV connector 130. The first channel 210 defines fluidic communication between the fluid reservoir 25 and the patient IV port 127/line 27, and the second channel 220 defines fluidic communication between the receptacle 110 and the fluid reservoir 25. The IV bag spike 120 further includes a first orifice 122-1 at an end of the first channel 210 and a second orifice 122-2 at an end of the second channel 220, such that each of the first orifice and the second orifice are in fluidic communication with the fluid reservoir 25 for fluidic transfer between the respective channels. In terms of the flow segments of FIG. 2, the second FS2 and third FS3 flow segments travel though separate ingress and egress orifices in the bag spike 120 between the IV connector 130 and the reservoir 25.

A vial 60 engaged in the receptacle 110 connects to the transfer channel 142 that leads to the second channel 220 and then into the bag spike 120 and attached IV bag or reservoir 25 for exchanging reconstitution fluid (saline solution) with the bag. The mixed, reconstituted medicine that has already been exclusively forced into the bag may now exit the bag and into the IV line 27 via the first channel 210. In operation, the flow control element 50 defines a fluidic path for transporting fluid from the vial to the patient IV line 27 that completely traverses the second channel 220 followed by the first channel 210. In this manner, the flow control element 50 imposes a fluidic barrier between the first channel 210 and the receptacle 110.

Figure 6:
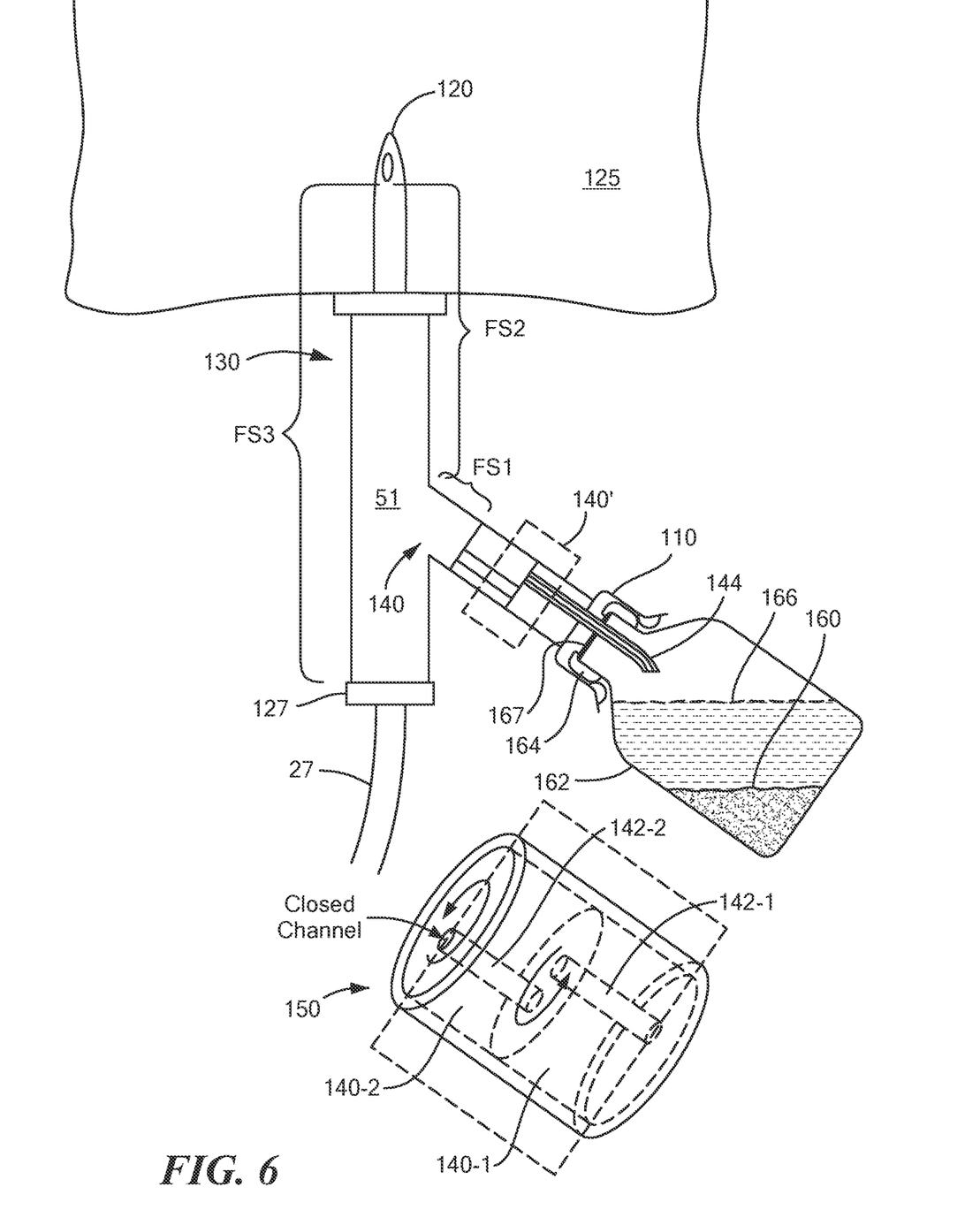
FIG. 6 shows a valve in the device of FIG. 4.

FIG. 6 shows a valve in the device of FIG. 1. During administration of a reconstituted drug, the powdered medication 160 arrives in a vial 162. The receptacle 110 has an apron and a spike 144 adapted for penetration of a resilient portion in a cap on the vial 162. The vial 162 has a collar 164 adapted for engagement by the receptacle 110, usually by a frictional and/or interference fit from subtle deformation of the resilient tabs on the receptacle 110. A puncture region 167 is an elastomeric or membrane material adapted for a sealing engagement with a cannulated spike 144 or needle that pierces the puncture region 167 for establishing fluid communication with the transfer channel 142 in the bifurcated junction body 140 that includes FS1 and FS2. Alternatively, a needleless or luer connector may connect to the vial 162.

Substantially concurrently, the IV connector 120 attaches to a saline solution bag 125. The IV connector 120 invokes the tapered end adapted for engaging a suitable IV saline solution bag 125. The fluid contents of the saline solution bag 125 provide both reconstitution fluid for the medication 160 and the IV fluid medium for patient transport. After attaching the saline solution bag 125, the connector 130 is inverted and the IV bag compressed to force saline solution into the vial 162 via FS1 and FS2. After a sufficient fluid level 166 is introduced into the vial 162, an assistant (nurse, technician) agitates the vial to reconstitute (mix) the saline solution and medication 160 into a solution or suspension. The connector 130/saline solution bag 125 combination is oriented with the vial 162 upwards so that the trapped air displaces up into the vial 162 and forces the reconstituted medicine down into the saline solution bag 125, again through FS2 and FS1, ideally defining a known medicinal concentration in the IV bag 125.

Conventional approaches leave this vial/bag combination in place for simply permitting the contents of the bag 125 to flow via a patient IV line 27 at an opposed end of the connector from the IV bag, as is common with IV delivery. Configurations herein dispose a valve 150 in the transfer channel 142 to define a fluidic separation from the vial 162 during the post-reconstitution medicinal delivery phase. This avoids subsequent introduction of any residual medication that may remain in the transfer channel 142 that could alter the concentration of the IV medication delivered to the patient.

In particular configurations, the valve 150 is to shut off the flow channel at the juncture of the transfer channel 142 and the IV flow channel 132 so that there is a reduced possibility of residual fluid in the transfer channel 142. The valve 150, therefore, may be located at the top of the fluid channel from the vial to the spike 144, as near the vial 162 as practicable. Alternatively, a valve 150 may be placed at the juncture of the transfer channel 142 and IV channel 132, discussed below, or at an intermediate position along the transfer channel 142 for facilitating manufacturing. Medication from the IV bag is then delivered via FS3, and cannot traverse back through FS1.

Figure 7:
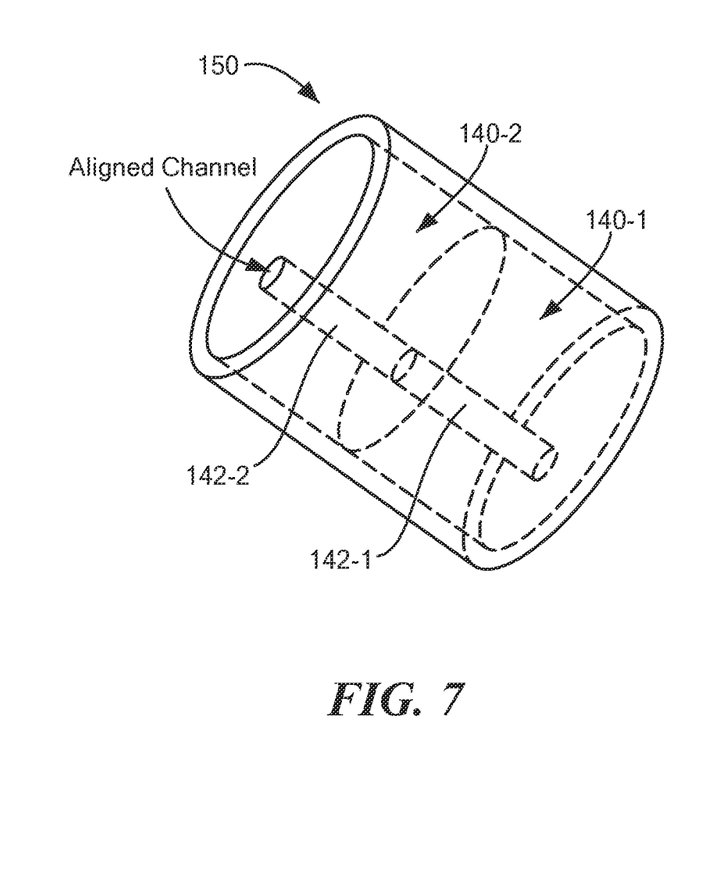
FIG. 7 shows an open valve in the device of FIG. 4.

FIG. 7 shows an open valve in the device of FIG. 6. The valve 150 may take the form of an off-center divided channel adapted for rotation in and out of alignment, shown exploded as dotted line segment 140'. Referring to FIGS. 6 and 7, the transfer channel 142 is defined by a vial side portion 142-1 and an IV side portion 142-2. The valve 150 further comprises concentric sections 140-1, 140-2 (140-N generally) of the bifurcated junction body 140 adapted to rotate individually for aligning the transfer channel 142 for fluid communication between the vial 162 and IV channel 132. The transfer channel 142 extends through the plurality of concentric sections 140 in the body, in which the concentric sections 140-N define a selectively opening passage depending on alignment of the channel portions 142-1 and 142-2. FIG. 7 shows an open valve in the device of FIG. 6 as the concentric sections 140 rotate to align the channel portions 142 for permitting saline solution mixing, reconstitution and reconstituted medicinal flow back into the IV saline solution bag 125.

Figure 8:
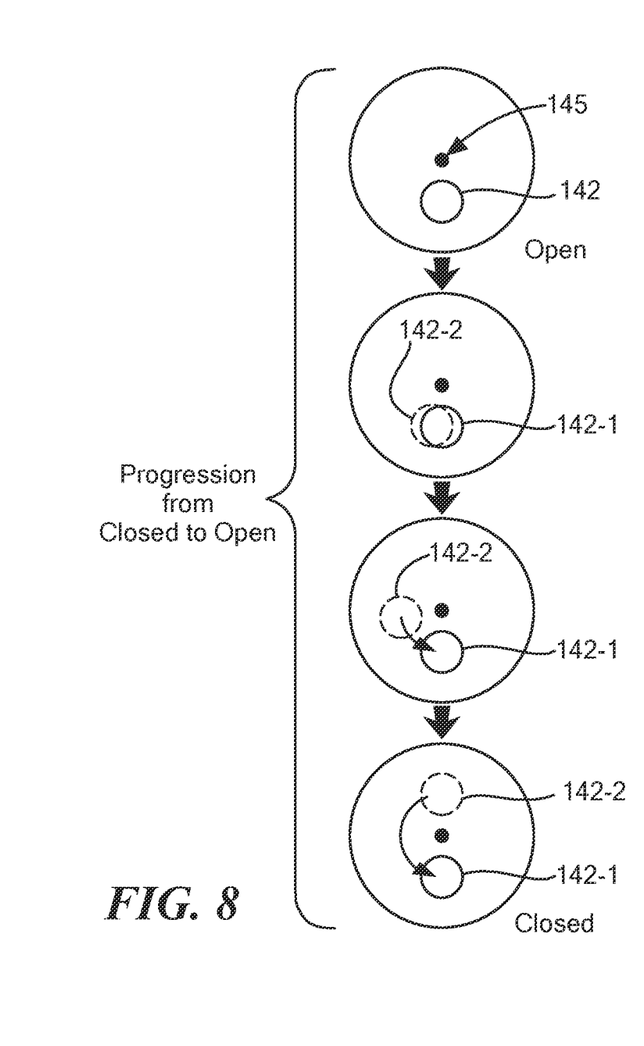
FIG. 8 shows an axial view of the valve in FIGS. 6 and 7 progressing between open and closed positions.

FIG. 8 shows an axial view of the valve in FIGS. 6 and 7 progressing between open and closed positions. The transfer channel 142 extends through a plurality of concentric sections 140 in the body, such that the concentric sections 140 define the valve and are adapted to rotate for aligning and unaligning the transfer channel 142. Unaligned concentric sections 140 act as a barrier and result in a discontinuous transfer channel as each portion 142 is blocked by the unaligned adjacent section 140-N.

The concentric sections 140 define the valve and are adapted to rotate for aligning and unaligning the transfer channel 142 as one concentric section 140-1 rotates relative to the other 140-2, and the transfer channel portion 142-2 is drawn out of alignment with the adjacent transfer channel portion based on the offset of the transfer channel portions from a rotational axis 145. The transfer channel 142 is therefore defined by the portions 142-1, 142-2 in each of the concentric sections 140, such that the portions are offset from a rotational axis 145 of the concentric sections for aligning the portions based on rotation of the concentric sections 140.

Figure 9:
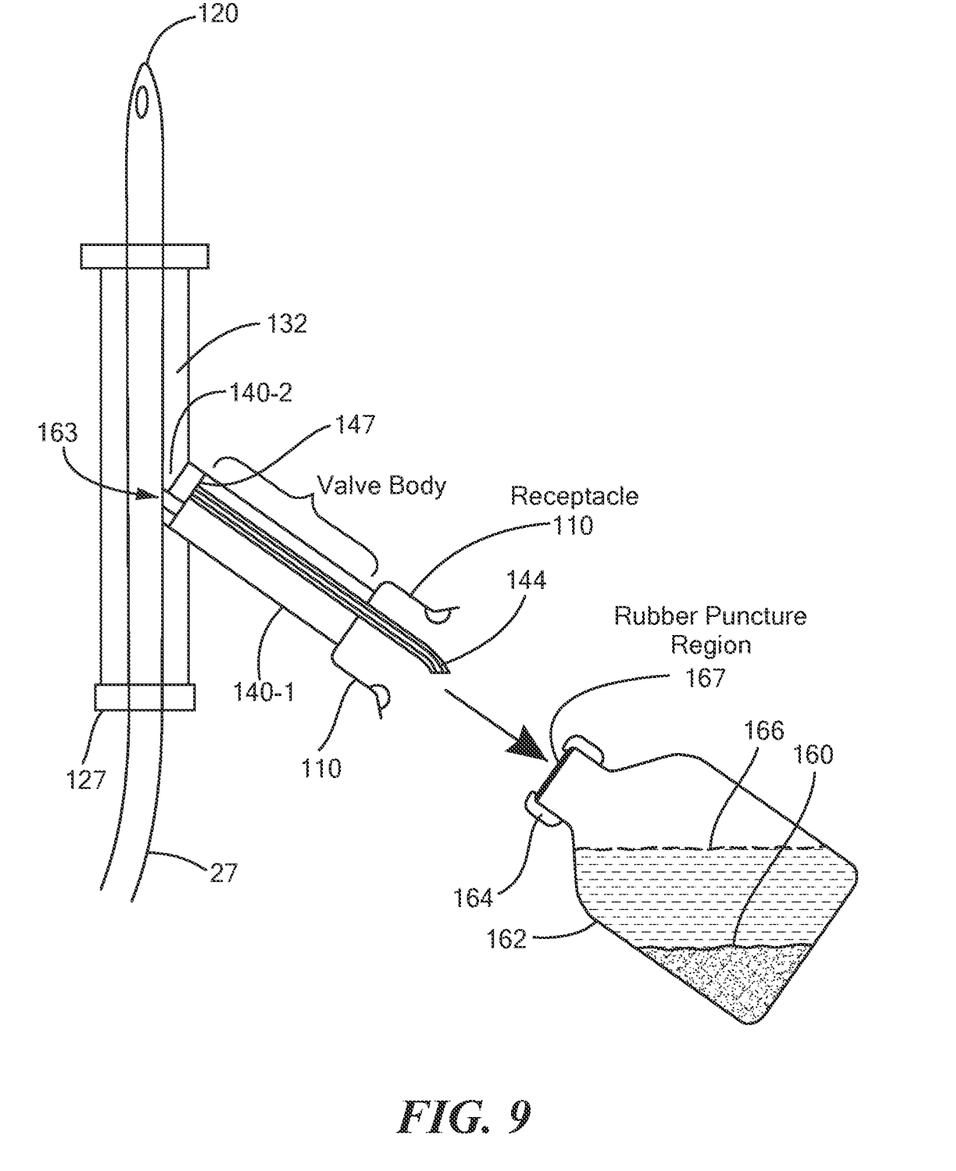
FIG. 9 shows an alternate valve implementation disposing the valve of FIGS. 6 and 7 at a protrusion in the IV stream for promoting drug mixing.

FIG. 9 shows an alternate valve implementation disposing the valve of FIGS. 6 and 7 at a protrusion in the IV stream for promoting drug mixing. FIG. 5 shows an alternate valve implementation disposing the valve of FIGS. 6 and 7 at a protrusion 163 in the IV stream for promoting drug mixing. In FIG. 9, a separation 147 between the IV side portion 140-2 and vial side portion 140-1 is disposed closer to the IV channel 132 such that it occupies a protrusion 163 in the IV channel 132. This arrangement reduces the length and volume of the channel portion 142-2 remaining in fluidic communication with the IV channel 132, minimizing a volume which could contain unmixed medication 160. Also, the protrusion 163 agitates the IV fluid flow to prevent any kind of vortex effect or current which could cause residual droplets or quantities of concentrated, reconstituted medication to remain. The construction of the juncture between the transfer channel 132 and IV channel 142 may therefore either be flush or exhibit the protrusion 163, depending on the location and construction of the valve 150.

Figure 10:
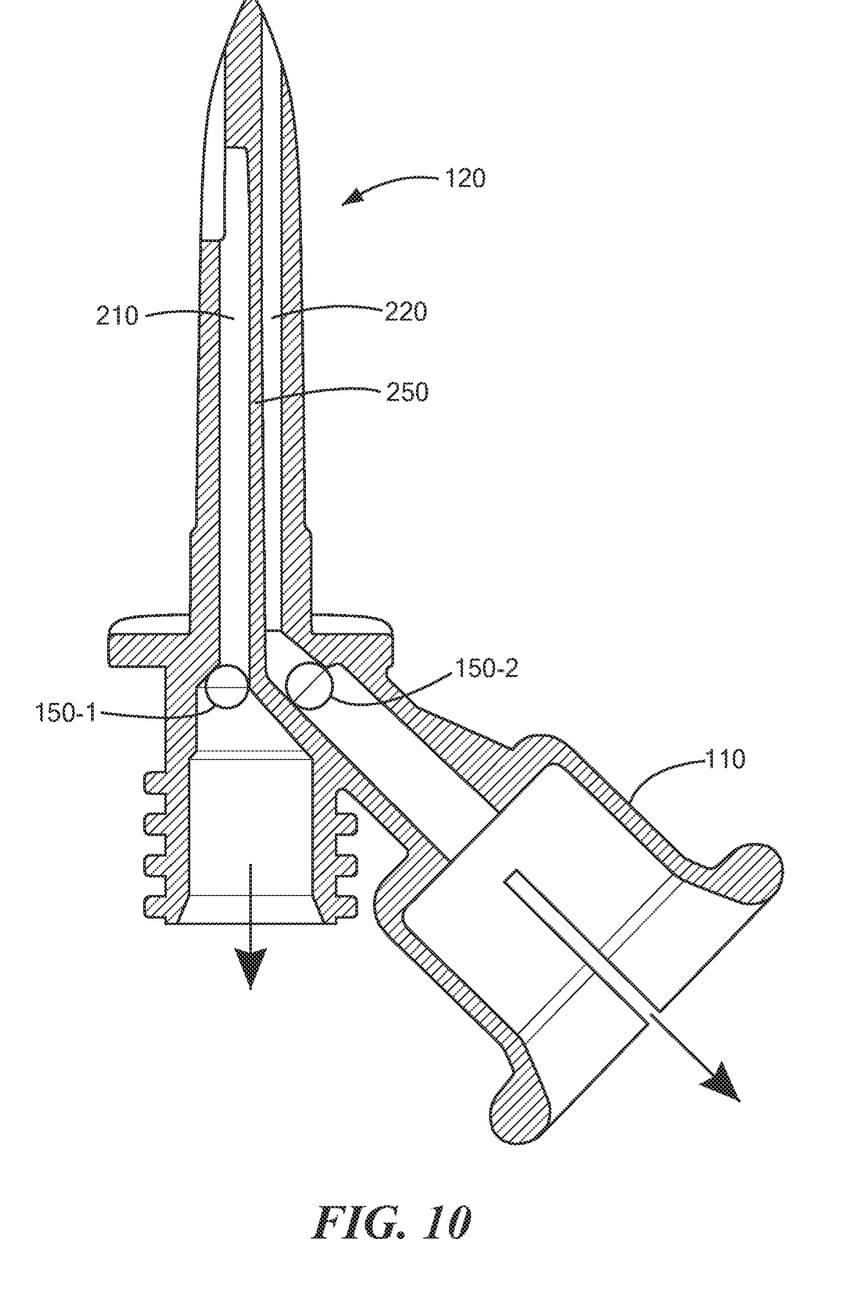
FIG. 10 shows a combined valve and partition (dual channel) arrangement of the reconstitution device.

FIG. 10 shows a combined valve and partition arrangement of the reconstitution device. Referring to FIGS. 2-5 and 10, the medicinal vial reconstitution and dispensing apparatus includes an IV bag spike 120 and the receptacle 110 adapted to engage a medicinal vial from the second channel extending through the IV bag spike 120. An intravenous (IV) connector 130 is adapted for inline connection to the patient IV line or IV set, such the IV connector is adapted for transport of medicinal fluids to a patient from the first channel 210 extending through the IV bag spike 120. The bifurcated junction body or ribbed housing extends from the bag spike to the IV connector and joins the receptacle for enclosing the first channel 210 and the second channel 220. The second channel 220 is adapted for fluidic communication between the receptacle 110 and the IV bag via the IV bag spike and the first channel 210 is configured for transferring liquids between the vial and IV connector.

One or more valves 150-1 . . . 150-2 in the connector 130 and/or bifurcated junction body 140 allow selectively opening and closing at least one of the first channel 210 and the second channel 220. As in the configuration of FIG. 4, a valve 150-2 on the second channel 220 is for sealing the medicinal vial 162. Alternatively or in addition, a valve 150-1 on the first channel 210 can seal the IV line from the bag, possible to ensure more complete mixing of the reconstituted medicine before patient delivery.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A medicinal vial reconstitution and dispensing apparatus, comprising:
a receptacle including an apron and a spike, the spike adapted to engage a medicinal vial and adapted for penetration of a resilient portion in a cap on the medicinal vial;
an intravenous (IV) connector adapted for inline connection to a patient IV line, the IV connector adapted for transport of medicinal fluids from a fluid reservoir to a patient via the patient IV line;
a bifurcated junction body extending from the IV connector to the receptacle, the bifurcated junction body having a transfer channel adapted for fluidic communication between the receptacle and the IV connector for transferring liquids between the vial and IV connector,
a flow control element for ensuing a controlled flow path through the IV connector, the controlled flow path directing fluid from the transfer channel to the fluid reservoir before passing to the patient IV line through the IV connector at an IV output;
a tapered end on the IV connector adapted for engaging an IV fluid bag defining the reservoir to establish fluidic communication between the IV connector and the fluid reservoir, the tapered end having at least one of the first and second orifices on a side of the tapered end, the first and second orifices defining respective fluidic connections to the patient IV line and the transfer channel,
the bifurcated junction body forming a continuous unitary reconstitution device with the IV connector formed from the tapered end to the IV output.

2. The apparatus of claim 1 wherein the flow control element divides fluid flow between an ingress channel and an egress channel to the fluid reservoir.

3. The apparatus of claim 1 wherein the IV connector has a textured region adjacent the tapered region for facilitating a frictional grasp during IV bag insertion.

4. The device of claim 1 wherein the bifurcated junction body and IV connector form a fluidically sealed vessel between the receptacle, IV connector and the fluid reservoir from the engaged vial.

5. The device of claim 1 wherein the IV connector and bifurcated junction body are formed from a single mold.

6. The device of claim 1 further comprising a flange and rib formed with the IV connector at a junction of the IV connector and the transfer channel, the junction formed more than half the length of the IV connector distal from a tip of the tapered end.

7. The device of claim 1 wherein the at least one of the first and second orifices is formed on an opposed side of the tapered end and more distal from a tip than the other of the first and second orifices for enforcing fluidic communication between the receptacle and the fluid reservoir.

8. The device of claim 7 wherein the orifice on the opposed side is defined by a side facing void in the tapered end.

9. The apparatus of claim 1 wherein the flow control element defines a plurality of fluidic flow segments though the IV connector, the fluidic flow segments traversed by medicinal fluid in the vial in a predetermined sequence the predetermined sequence including:
- a first flow segment from a transfer channel ingress to the IV connector via the transfer channel,
- a second flow segment from the transfer channel into the fluid reservoir, and
- a third flow segment from the fluid reservoir to the patient IV line through the IV connector, the flow control element disposed for directing fluid from the first flow segment to the second flow segment prior to the fluid traversing the third flow segment.

10. The apparatus of claim 9 wherein the first and second flow segments direct fluid in opposed directions though the IV connector.

11. The apparatus of claim 10 wherein the second and third flow segments travel though separate ingress and egress orifices between the IV connector and the reservoir.

12. The apparatus of claim 11 wherein the IV connector has separate channels defined by the flow control element, each channel corresponding to one of the second or third flow segments.

13. The apparatus of claim 1 wherein the flow control element defines a first channel and a second channel through the IV connector,
- the first channel defining fluidic communication between the fluid reservoir and the patient IV line; and
- the second channel defining fluidic communication between the receptacle and the fluid reservoir.

14. The apparatus of claim 13 wherein the flow control element defines a fluidic path for transporting fluid from the vial to the IV output that completely traverses the second channel followed by the first channel.

15. The apparatus of claim 13 wherein the flow control element directs a fluidic path from the vial through the reservoir prior to fluidic flow into the IV output.

16. The apparatus of claim 13 wherein the bifurcated junction body encloses the first channel and the second channel,
- the IV connector including an IV bag spike adapted for insertion into an IV bag defining the fluid reservoir, the second channel adapted for fluidic communication between the receptacle and the IV bag via the IV bag spike and the first channel adapted for transferring liquids between the IV bag and IV connector via the IV bag spike when inserted into the IV bag.

17. The apparatus of claim 16 wherein the IV bag spike further includes a first orifice at an end of the first channel and a second orifice at an end of the second channel, each of the first orifice and the second orifice in fluidic communication with the fluid reservoir for fluidic transfer between the respective channels.

18. A medicinal vial reconstitution and dispensing apparatus, comprising:
- an IV bag spike;
- a receptacle including an apron and a vial spike adapted to engage a medicinal vial from a second channel extending through the IV bag spike, the vial spike adapted for penetration of a resilient portion in a cap on the medicinal vial;
- an intravenous (IV) connector adapted for inline connection to a patient IV line, the IV connector adapted for transport of medicinal fluids to a patient from a first channel extending through the IV bag spike; and
- a bifurcated body extending from a longitudinal side of the IV connector to the receptacle, the bifurcated body enclosing the first channel and the second channel, the second channel adapted for fluidic communication between the receptacle and an IV bag via a second orifice on the IV bag spike and the first channel for transferring liquids between the IV bag and an IV output on the IV connector via a first orifice on the IV bag spike when inserted in an IV bag;
- a tapered end on the IV connector adapted for engaging the IV bag defining the reservoir to establish fluidic communication between the IV connector and the fluid reservoir, the tapered end having at least one of the first and second orifices on a side of the tapered end, the first and second orifices defining respective fluidic connections to the patient IV line and the receptacle,
- the bifurcated junction body forming a continuous unitary reconstitution device with the IV connector formed from the tapered end to the IV output.

\* \* \* \* \*